United States Patent [19]
Hubbell et al.

[11] Patent Number: 5,758,538
[45] Date of Patent: Jun. 2, 1998

[54] TENSIOMETER AND METHOD OF DETERMINING SOIL MOISTURE POTENTIAL IN BELOW-GRADE EARTHEN SOIL

[75] Inventors: Joel M. Hubbell, Idaho Falls, Id.; Earl D. Mattson, Albuquerque, N. Mex.; James B. Sisson, Idaho Falls, Id.

[73] Assignee: Lockheed Martin Idaho Technologies Company, Idaho Falls, Id.

[21] Appl. No.: 391,942

[22] Filed: Feb. 21, 1995

[51] Int. Cl.$^6$ .................................................. G01L 11/00
[52] U.S. Cl. ............................................................. 73/73
[58] Field of Search .......................... 73/73, 862.391, 73/19.9, 23.2, 29.01, 19.05, 19.09, 29.02, 29.03, 335.02

[56] References Cited

U.S. PATENT DOCUMENTS

| | | | |
|---|---|---|---|
| 2,878,671 | 3/1959 | Prosser et al. | 73/73 |
| 3,045,477 | 7/1962 | Matson | 73/73 |
| 3,049,914 | 8/1962 | Richards | 73/73 |
| 3,871,211 | 3/1975 | Tal | 73/73 |
| 3,898,872 | 8/1975 | Skaling et al. | 73/73 |
| 3,910,300 | 10/1975 | Tal | 73/73 |
| 3,939,699 | 2/1976 | McCormick | 73/73 |
| 4,068,525 | 1/1978 | Skaling | 73/73 |
| 4,332,172 | 6/1982 | Torstensson | 73/73 |
| 4,408,481 | 10/1983 | Sidey | 73/73 |
| 4,453,401 | 6/1984 | Sidey | 73/73 |
| 4,520,657 | 6/1985 | Marthaler | 73/73 |
| 4,922,945 | 5/1990 | Browne | 73/73 |
| 5,508,947 | 4/1996 | Sierk et al. | 73/1 B |

FOREIGN PATENT DOCUMENTS

| 214929 | 10/1994 | Germany | 73/73 |
|---|---|---|---|

OTHER PUBLICATIONS

Morrison, Robert D., et al., *A Tensiometer and Pore Water Sampler for Vadose Zone Monitoring*. Soil Science, Nov. 1987, vol. 144, No. 5, pp. 367–372.

James, M. L., et al., *Applied Numerical Methods for Digital Computation*, Third Edition, pp. 86–93 no date.

*Primary Examiner*—Thomas B. Will
*Assistant Examiner*—Andrew Hirshfeld
*Attorney, Agent, or Firm*—Wells St John Roberts Gregory & Matkin

[57] ABSTRACT

A tensiometer to in situ determine below-grade soil moisture, potential of earthen soil includes, a) an apparatus adapted for insertion into earthen soil below grade, the apparatus having a below-grade portion, and, comprising; b) a porous material provided in the below-grade portion, the porous material at least in part defining a below-grade first fluid chamber; c) a first fluid conduit extending outwardly of the first fluid chamber; d) a first controllable isolation valve provided within the first fluid conduit, the first controllable isolation valve defining a second fluid chamber in fluid communication with the first fluid chamber through the first fluid conduit and the isolation valve, the first controllable isolation valve being received within the below-grade portion; and e) a pressure transducer in fluid communication with the first fluid chamber, the pressure transducer being received within the below-grade portion. An alternate embodiment includes an apparatus adapted for insertion into earthen soil below grade, the apparatus having a below-grade portion, and including: i) a porous material provided in the below-grade portion, the porous material at least in part defining a below-grade first fluid chamber; and ii) a pressure sensing apparatus in fluid communication with the first fluid chamber, the pressure sensing apparatus being entirely received within the below-grade portion. A method is also disclosed using the above and other apparatus.

1 Claim, 6 Drawing Sheets

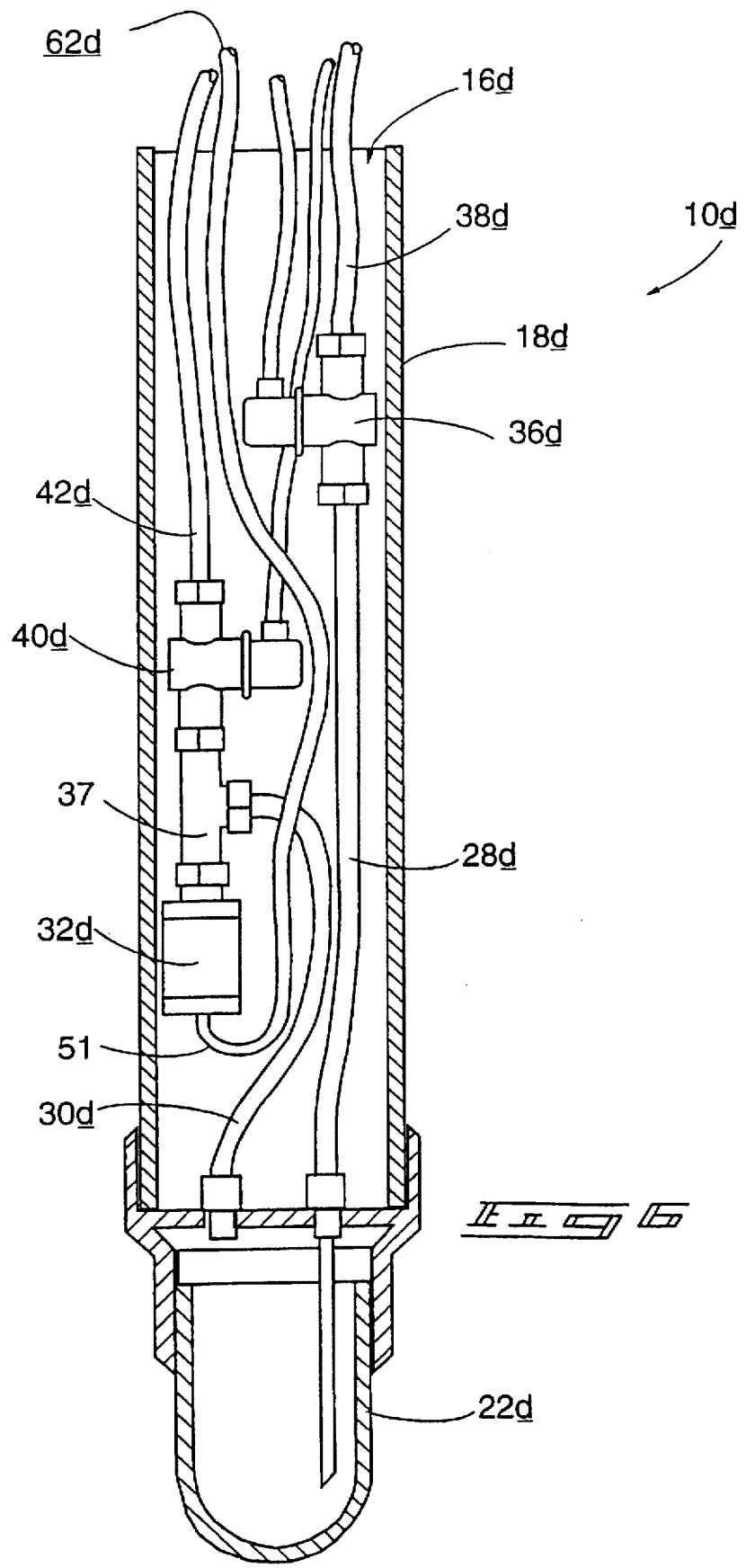

TENSIOMETER AND METHOD OF DETERMINING SOIL MOISTURE POTENTIAL IN BELOW-GRADE EARTHEN SOIL

CONTRACTUAL ORIGIN OF THE INVENTION

The United States Government has rights in this invention disclosed under contract number DE-AC07-76ID01570 between the U.S. Department of Energy and EG&G Idaho, Inc., now contract number DE-AC07-94ID13223 with Lockheed Idaho Technologies Company.

TECHNICAL FIELD

This invention relates to tensiometers and to techniques for measuring soil moisture potential using tensiometers.

BACKGROUND OF THE INVENTION

If the moisture potential of soil can be accurately monitored, irrigation can be controlled to optimize the rate of plant growth. One type of instrument for measuring soil moisture potential is a tensiometer. A conventional tensiometer comprises a sealed tube defining a chamber which is normally completely filled with water, a hollow porous tip on one end of the tube, and a vacuum gauge connected to the water chamber. The porous tip is inserted in the soil, and establishes liquid contact between the water in the tube and moisture in the soil surrounding the tip. Relatively dry soil tends to pull water from the tube through the porous tip. However since the tube is sealed, only a minute amount of water is actually withdrawn. Accordingly, the water in the tube is placed under tension by the pulling effect of the dry soil, thus creating a measurable subatmospheric pressure in the tube. Higher moisture contents in the soil produce correspondingly less vacuum in the tube, and completely saturated soil registers substantially zero vacuum or atmospheric pressure.

Typical tensiometer constructions provide a tube or column of water which extends from the porous tip to above grade. It will be apparent that the deeper the porous tip is buried, the longer the column of liquid above it will become.

Air presence in the water reservoir during tensiometric measurement is undesirable. Air can enter the reservoir by diffusing through the porous tip. More commonly, dissolved air present in the water that enters the vessel comes out of solution in the reduced pressure environment of the tensiometer. Eventually, the entire tensiometer would become filled with air. Air will increase the time required to reach pressure equilibrium because large volumes of water must move through the porous tip to effect the mass transfer of air through the tip. Thus in order to obtain accurate readings, the water and air are desirably purged periodically from the tensiometer reservoir and replaced with degassed water.

To facilitate purging of air from the tensiometer reservoir, a conventional tensiometer is typically provided with a column of water connecting a surface located pressure measuring device to the soil-embedded porous tip. However, there is a physical limit to the length of a column of water which can be supported by atmospheric pressure (about 1000 cm at sea level), and the useful measurement range of the tensiometer is reduced as the column of water above the porous tip is lengthened. The pressure exerted by the column of water increases the pressure in the porous tip, which in turn increases the apparent soil moisture tension recorded by the above-surface pressure measuring device.

For example, the pressure in the porous tip increases in direct proportion to the length of the column of water. This gives falsely low readings of soil moisture tension at the pressure-measuring device at the surface. Conventional tensiometers are limited to use at depths of less than about 750 cm. In addition, since the pressure-measuring device is located above the earth's surface, both the pressure-measuring device and the column of water in hydraulic communication with the porous tip are subject to daily temperature changes unless they are housed in an insulated structure.

There remains a need for methods of monitoring soil moisture potential deep within sub-grade earthen soil, and for devices which facilitate such measurements. Although a principal motivation for this invention arose from concerns associated with deep soil use of tensiometers, the artisan will appreciate inventive other uses of the invention which is only intended to be limited by the accompanying claims appropriately interpreted in accordance with the Doctrine of Equivalents.

BRIEF DESCRIPTION OF THE DRAWINGS

Preferred embodiments of the invention are described below with reference to the following accompanying drawings.

FIG. 6 is a side diagrammatic sectional view of a reduction-to-practice embodiment tensiometer apparatus in accordance with the invention.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

In accordance with one aspect of the invention, a tensiometer to in situ determine below-grade soil moisture potential of earthen soil comprises:

an apparatus adapted for insertion into earthen soil below grade, the apparatus having a below-grade portion, and comprising:

a porous material provided in the below-grade portion, the porous material at least in part defining a below-grade first fluid chamber;

a first fluid conduit extending outwardly of the first fluid chamber;

a first controllable isolation valve provided within the first fluid conduit, the first controllable isolation valve defining a second fluid chamber in fluid communication with the first fluid chamber through the first fluid conduit and the isolation valve, the first controllable isolation valve being received within the below-grade portion; and a pressure transducer in fluid communication with the first fluid chamber, the pressure transducer being received within the below-grade portion.

In accordance with another aspect of the invention, a tensiometer to in situ determine below-grade soil moisture potential of earthen soil comprises:

an apparatus adapted for insertion into earthen soil below grade, the apparatus having a below-grade portion, and comprising:

a porous material provided in the below-grade portion, the porous material at least in part defining a below-grade first fluid chamber; and a pressure sensing apparatus in fluid communication with the first fluid chamber, the pressure sensing apparatus being entirely received within the below-grade portion.

In accordance with still another aspect of the invention, a method of monitoring soil moisture potential in below-grade earthen soil comprises the following steps:

providing a tensiometer having a porous member, a first fluid chamber defined at least in part by the porous member, a pressure transducer in fluid communication with the first fluid chamber, and a first fluid conduit in fluid communication with the first fluid chamber;

placing the tensiometer within earthen soil below grade to position the porous member in hydraulic contact with earthen soil, the pressure transducer being positioned below grade;

providing a degassed liquid within the tensiometer first fluid chamber through the first fluid chamber and hydraulically sealing the degassed liquid within the first fluid chamber but for the porous member;

permitting the degassed liquid to permeate said porous member to cause a change in pressure in the first fluid chamber; and determining the change in pressure with the pressure transducer.

Figure 1:
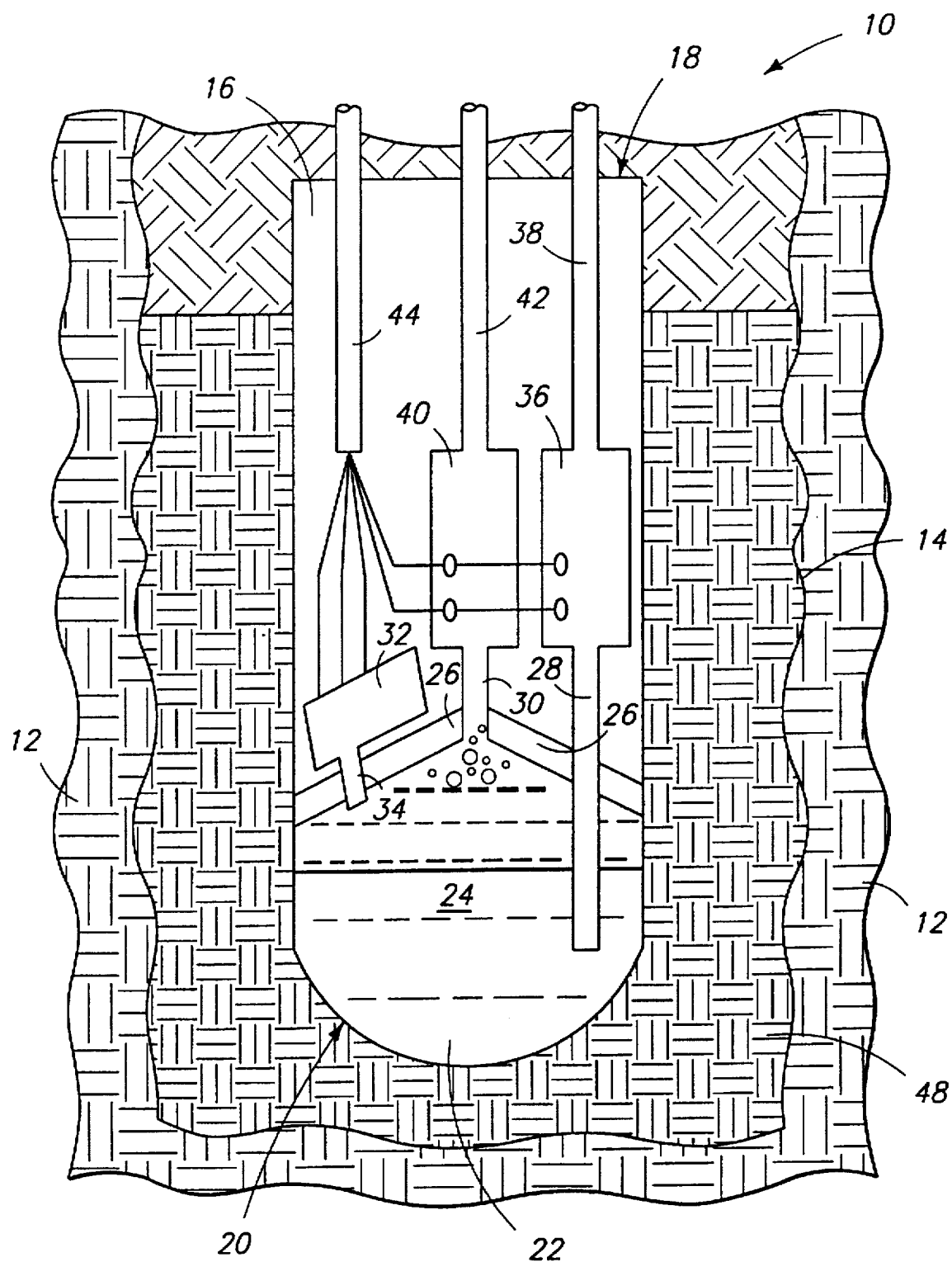
FIG. 1 is a side diagrammatic or schematic view of a tensiometer apparatus in accordance with the invention.

More particularly and first with reference to FIG. 1, a tensiometer in accordance with one aspect of the invention is indicated generally by reference numeral 10. Such comprises an apparatus adapted for insertion into earthen soil 12 below grade within a bore or hole 14 provided therein. The illustrated portion of apparatus 10 in FIG. 1 is received entirely below grade, and accordingly constitutes a below-grade portion. Apparatus 10 includes an elongated housing 16 which retains various apparatus components. Housing 16 comprises an upper end 18 and a lower end 20. A porous material tip 22 is provided at lower end 20 and in part defines a first fluid chamber 24 within housing 16. A pair of upwardly angled walls 26 join at an apex, and define an upper region for first fluid chamber 24. A first fluid conduit 28 extends outwardly of first fluid chamber 24 through one of walls 26, while a second fluid conduit 30 extends outwardly of first fluid chamber 24 at the apex where walls 26 meet. A pressure transducer 32 is provided upwardly and outwardly of first fluid chamber 24, and is in fluid communication therewith through a conduit 34 extending through one of walls 26.

A first controllable isolation valve 36 is provided within first fluid conduit 28. Such defines a second fluid chambers or tube 38 which is in fluid communication with first fluid chamber 24 through first fluid conduit 28 and isolation valve 36. In the illustrated embodiment, second fluid chamber 38 is in the form of polyethylene tubing extending upwardly and outwardly of housing 16 to an above-grade location. Isolation valve 36 is preferably positioned as shown in close proximity to first fluid chamber 24 and porous material 22, for example within three feet of the lowestmost outward portion of porous material 22. Ideally, the proximity would be within inches.

A second controllable valve 40 is provided within second fluid conduit 30. Tubing 42 extends upwardly and outwardly therefrom through housing 16 and extends to an above-grade location. Another tube 44 extends outwardly of housing 16 to an above-grade location, and houses the various illustrated wires for controlling electronic valves 36 and 40, and for obtaining readings from pressure transducer 32. Housing 16 constitutes a common below-grade housing which retains the illustrated components in a sealed, air-tight manner.

To operate device 10, housing 16 with its associated tubing 38, 42 and 44 would be placed within earthen bore 14 to position porous member 22 in hydraulic contact with earthen soil. Tubes 38, 42 and 44 would extend to a location out of bore 14, above grade. Preferably, bore 14 is first provided with a fine silica flour backfill material 48 surrounding porous member 22. Such facilitates establishing effective hydraulic contact between porous material 22 and fluid within chamber 24 and soil at the base (not shown) of bore 14. Accordingly in one aspect of the invention, pressure transducer 32 and isolation valves 36 and 40 are positioned below grade and in close proximity to first fluid chamber 24.

To initiate the device, valves 36 and 40 would be opened. Tube 38 would be connected with a source of degassed liquid, while tube 42 would extend to a fluid collection container. Degassed liquid would be provided within tensiometer apparatus 10 through tube 38, open first valve 36, and first fluid conduit 28 to within first fluid chamber 24. Most typically the degassed liquid utilized in all tensiometers is water. Water, and any bubbles formed therein, would flow outwardly through second conduit 30, through open second controllable isolation valve 40, and through conduit 42 to a collection chamber above ground. Thereafter, isolation valves 36 and 40 would be activated to close, thereby effectively isolating chamber 24 from atmospheric pressure and the head of water thereabove. Degassed liquid within chamber 24 will then permeate porous member 22 as necessary to reach equilibrium with the surrounding soil, and thereby cause some change in the pressure within first fluid chamber 24. Such change will be determined by pressure transducer 32 and relayed via the illustrated wires to an indicator located above grade.

Note an advantage of the invention in providing a valve below grade in close proximity to fluid chamber 24 being the elimination of an otherwise long, prior art column of water extending above the porous material. Isolation valve 36 effectively precludes a column of water from impacting operation of the device when valve 36 is closed. Second isolation valve 40 would, accordingly, also be closed during tensiometric operation.

During operation, air bubbles may manifest within first fluid chamber 24. Accordingly as desired, first and second controllable valves 36, 40 can be periodically opened and fluid chamber 24 flushed as described above with other degassed liquid. Such could also be automatically controlled to occur at designated intervals.

The above-described apparatus can also be calibrated in situ. For example, first fluid chamber 24 can be filled with a gas to a first known pressure. Immediately after the filling, a calibration pressure of the gas within first fluid chamber 24 is measured with transducer 32, and compared to the known pressure for purposes of calibration.

The device facilitates deep tensiometric measurements by eliminating a long column of water which directly interfaces with chamber 24. However, as will be appreciated by the artisan, the device also has significant utility in sensing soil moisture potential in soil of shallow depths as well. The device can also sense positive pressures if the water saturation level is higher than the transducer.

Figure 2:
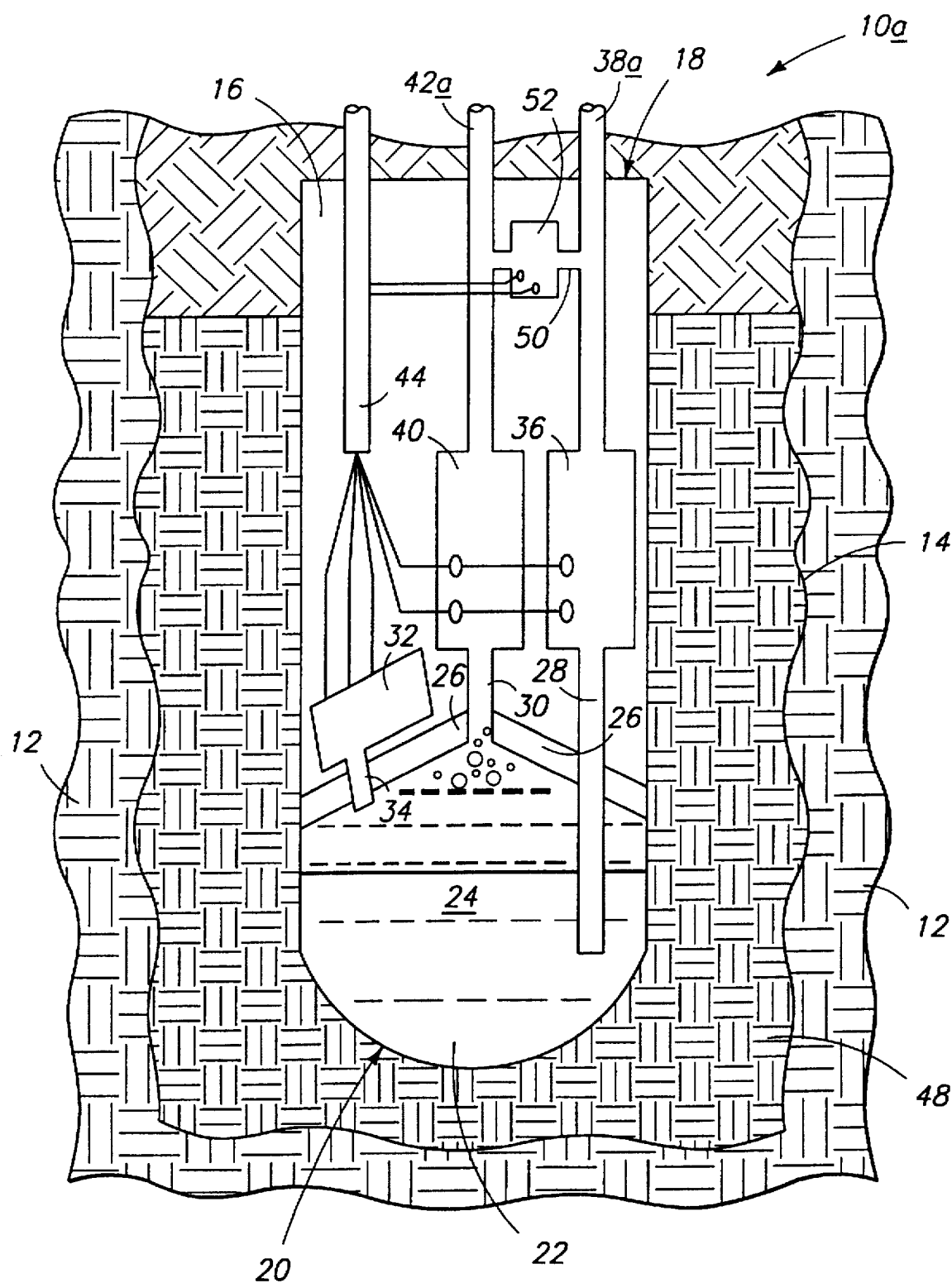
FIG. 2 is a side diagrammatic or schematic view of an alternate embodiment tensiometer apparatus in accordance with the invention.

An alternate embodiment tensiometer apparatus 10a is described with reference to FIG. 2. The same numerals from FIG. 1 are utilized where appropriate, with "a" as a suffix being utilized to designate differences. Tensiometer 10a is provided with a flushing third conduit 50 which effectively extends between the first fluid conduit and the second fluid conduit outside of first fluid chamber 24 and above valves 36 and 40. In the illustrated and preferred embodiment, flushing third fluid conduit 50 extends between conduits 38a and 42a, with a third controllable valve 52 being provided therewithin. In filling or air flushing operation as described above, valve 52 would remain closed. However to flush liquid from lines 38a and 42a above conduit 50, valve 52 would be energized to open while valves 40 and 36 would be closed. Gas under pressure would be pumped through conduit 38a to flush liquid therefrom outwardly through flushing conduit 50, third valve 52, and outwardly of conduit 42a. Such provides the advantage of enabling complete removal of liquid from tubes 42a and 38a above conduit 50 and valve 52. This might be desirable in freezing conditions to avoid freezing of water within lines 38a and 42a. Such also provides an apparatus and operation wherein all degassed liquid of the tensiometer apparatus in tensiometric operation is received entirely below grade.

Figure 3:
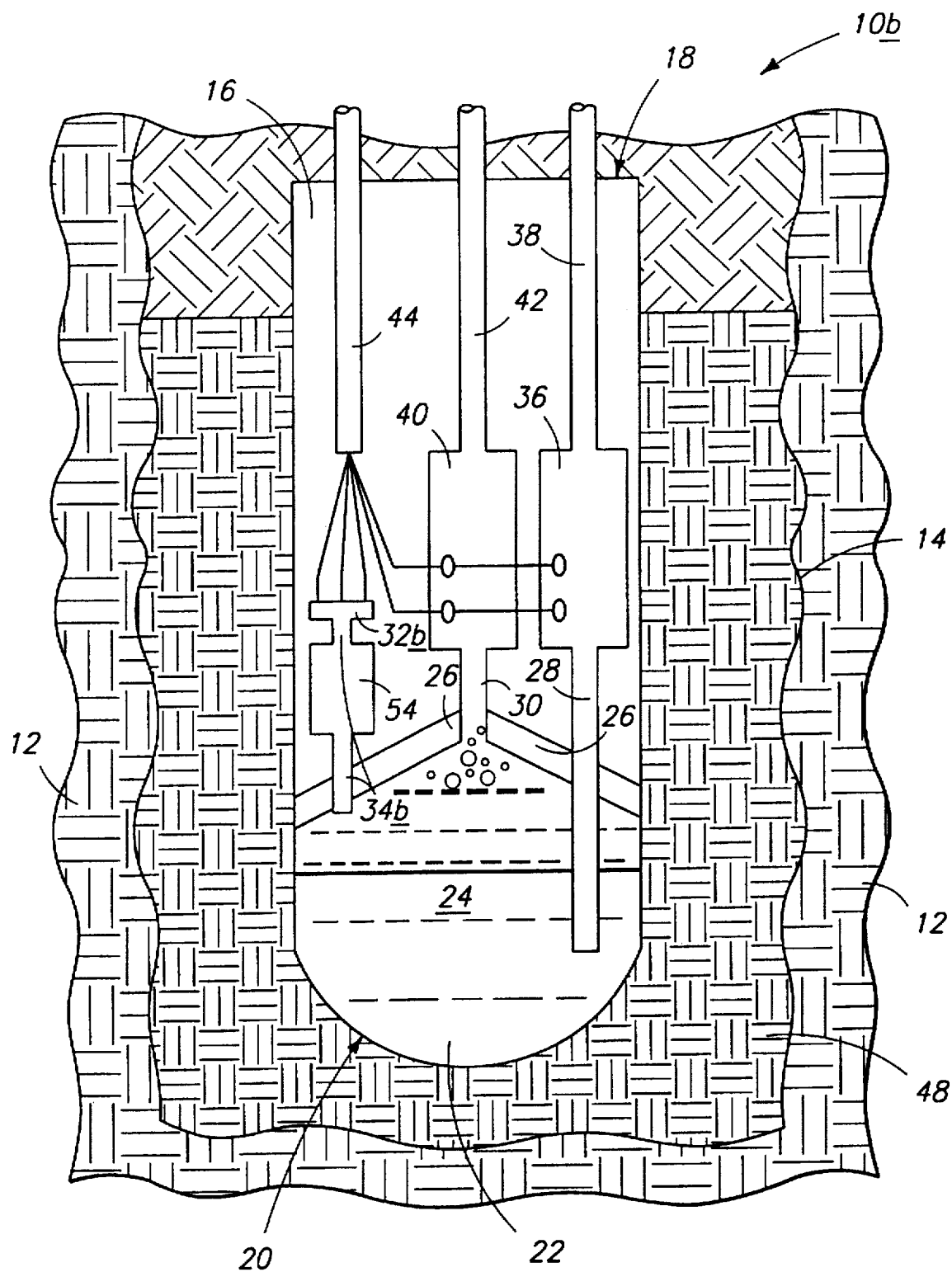
FIG. 3 is a side diagrammatic or schematic view of yet another alternate embodiment tensiometer apparatus in accordance with the invention.

FIG. 3 illustrates yet another alternate embodiment tensiometric apparatus 10b. Again, like numbers from the FIG. 1 embodiment are utilized, but for addition of a "b" suffix to designate differences. In this embodiment, transducer conduit 34b is provided with a transducer isolation valve 54, which is effectively positioned between transducer 32b and first fluid chamber 24. Such is preferably included to provide isolation of and thereby prevent potential damage to transducer 32b. For example, most transducers are designed to operate over a narrow pressure range and can be damaged if subjected to pressures outside that range. When the device is used for deep tensiometric measurements, opening of valves 36 and 40 will subject fluid within chamber 24 (and correspondingly transducer 32) to extremely high pressures the result of the head from the column of water extending to the surface of the soil. To prevent potential damage to the transducer, transducer isolation valve 54 would normally be closed when valves 36 or 40 were opened, except during calibration.

Figure 4:
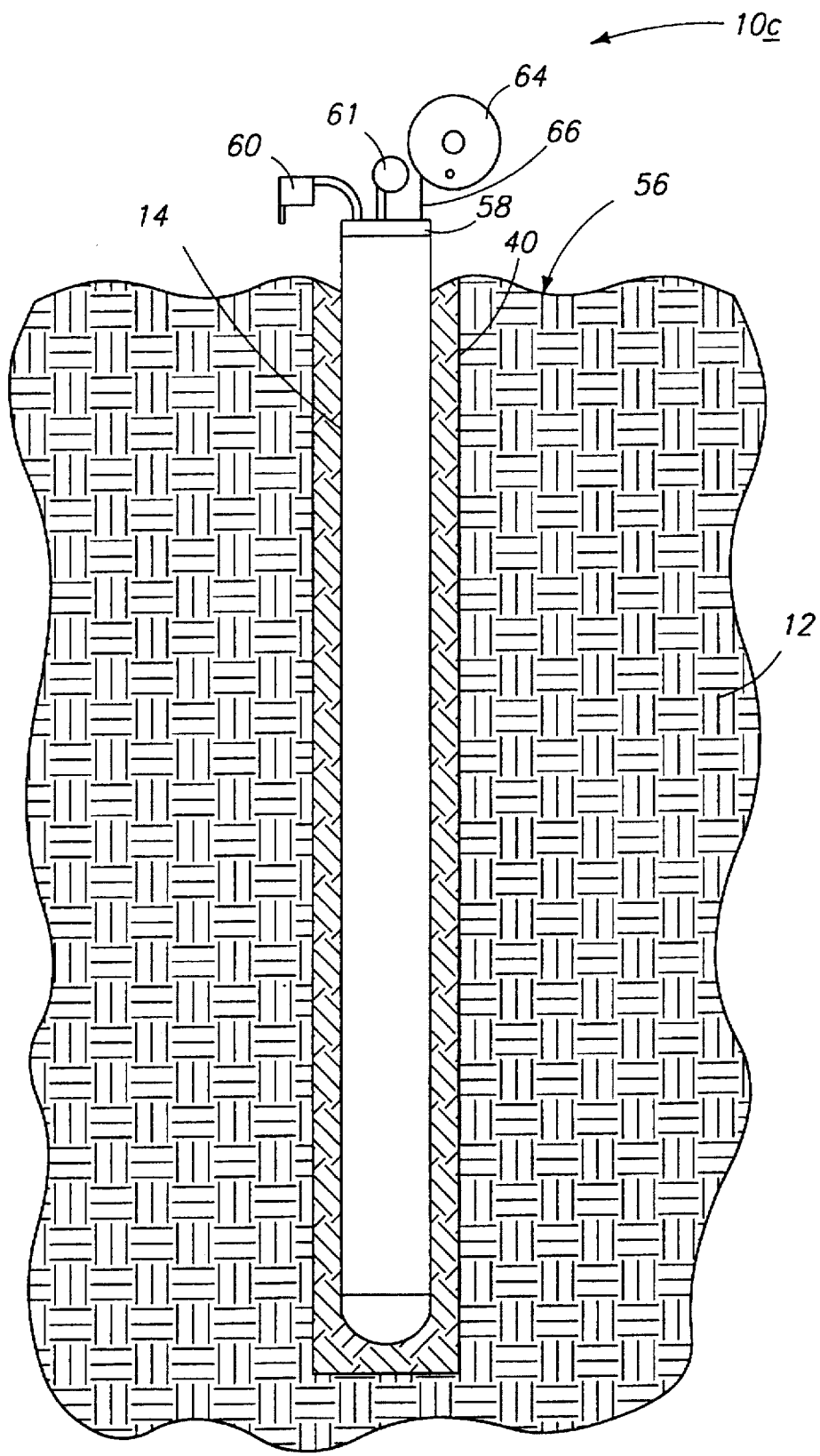
FIG. 4 is a diagrammatic section of yet another alternate embodiment tensiometer apparatus in accordance with the invention, and is shown inserted into earthen soil.
Figure 5:
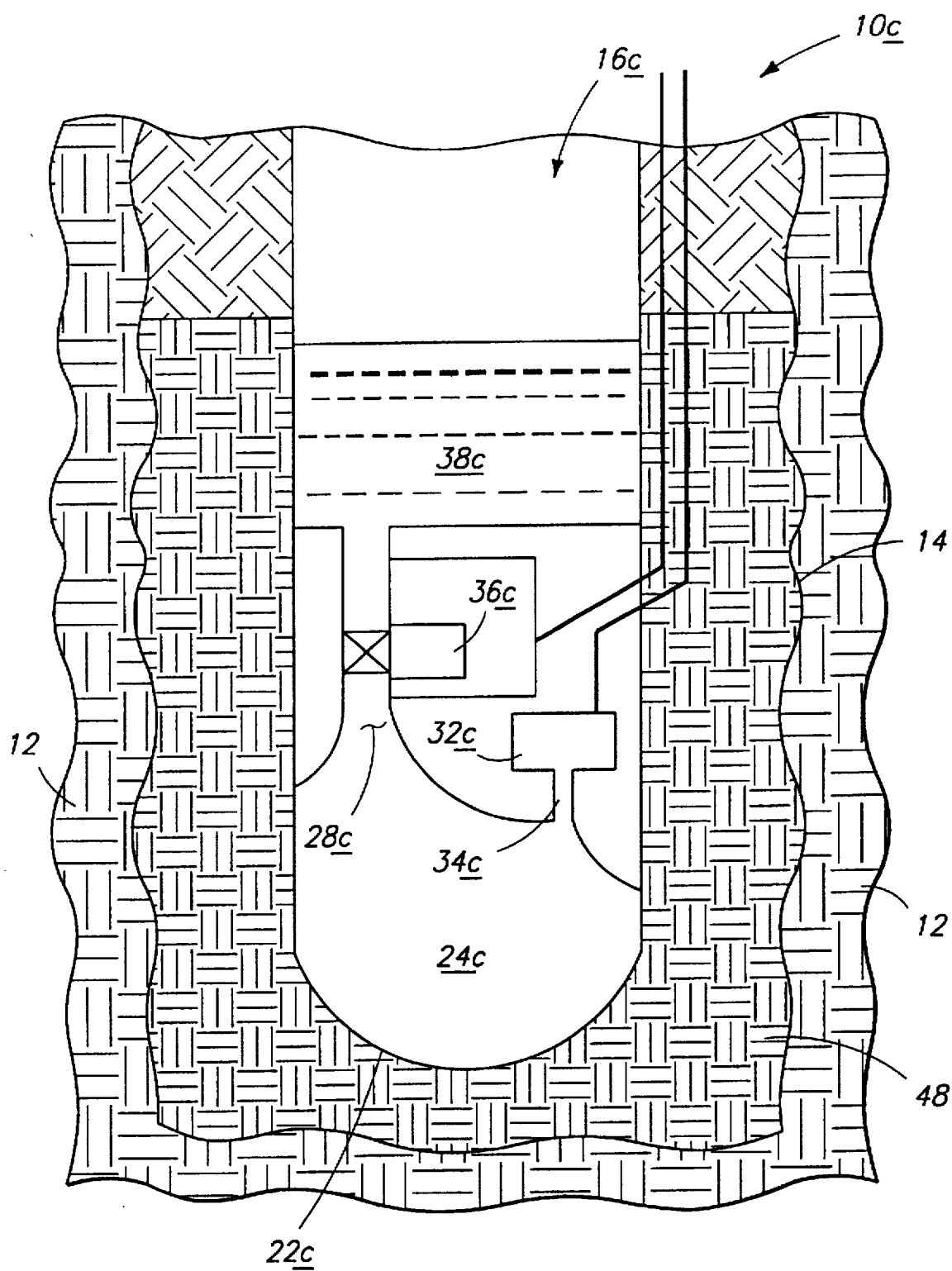
FIG. 5 is an enlarged view of a portion of the FIG. 4 apparatus showing internal workings.

FIGS. 4 and 5 diagrammatically illustrate yet another embodiment 10c whereby a single-valve tensiometer is utilized for deep tensiometer measurements. Like numbers are utilized from FIG. 1, with differences being denoted by the suffix "c". First fluid chamber 24c is defined by a porous material 22c provided at the end of a modified housing 16c which extends all the way to above-grade level 56. First isolation valve 36c is provided within first fluid conduit 28c to effectively define a second fluid chamber 38c above first fluid chamber 24c. Accordingly in this embodiment, controllable isolation valve 36c is the only below-grade valve of the tensiometer. In operation, isolation valve 36c is closed to isolate first fluid container 24c from second fluid chamber 38c. The depth of water within chamber 38c is preferably kept to less than a few feet, so the effective measurement range for the device in operation is unaffected by depth of the installation.

Tensiometer apparatus 10c is placed in a borehole 14 and backfilled as previously described. Housing 16c, which is effectively in the form of elongated PVC tubing, extends upwardly and outward of soil surface 56. A small volume of water is poured from land surface into tubing 38c, and valve 36c is opened to allow water to move into first fluid reservoir 24c. A sealing cap 58 (FIG. 4) is provided atop housing 16c. Entrapped air in reservoir 24c can be removed by application of vacuum to within housing 16c. Specifically, a vacuum pump 60 is provided and communicates through sealing cap 58 to within tubular housing 16c. Following evacuation of air in tubular housing 16c, degassed water is allowed into tubular housing 16c which forces the air out of the lower chamber of the tensiometer. Valve 36c is then closed, and the water in reservoir 24c typically goes out through porous material 22c into surrounding sediment until pressure in the tensiometer and adjoining sediment are in equilibrium. Valve 36c again isolates water contained in chambers 38c and 24c so that pressure can build up within chamber 24c and be sensed by transducer 32c, with data stored via some data logger (not shown). Head pressure from reservoir 38c thereby is immaterial after valve 36c is closed and equilibrium is reached.

The single valve deep tensiometer 10c can be calibrated in place using a vacuum gauge 61 (FIG. 4). For example, cap 58 is removed and a water-level recorder 64 (FIG. 4) is lowered to measure water level within reservoir 38c using a line or level tape 66 (FIG. 4 only). Water level tape 66 is removed from tubular housing 16c, and cap 58 replaced to produce a fluid-tight seal. Valve 36c is opened and pressure varied in tubular housing 16c using vacuum pump 60, while measurements are determined from vacuum reference gauge 61. Correlation of data from reference gauge 61 and pressure transducer 32c is used to produce a calibration curve.

An alternate and reduction-to-practice example 10d is shown in FIG. 6. Again, like numerals are utilized from the FIG. 1 embodiment with differences being designated with a suffix "d". Housing 16d comprises a rigid, 12-inch long cylinder attached to a one-bar porous ceramic cup 22d approximately 2½ inches in length and 1.9 inches in diameter. Porous cup 22d is suitably attached to housing 16d utilizing an epoxy adhesive or cement, or via a compression fitting. First fluid conduit 30d extends to a "T" interconnection 37. Transducer 32d connects to one side of "T" connector 37, while a first isolation valve 40d connects to the opposing end. An example suitable pressure transducer is Model ST2P15G1, having a range of from +15 to −15 psig, sold by SenSym of Milpitas, Calif. An electric cable 51 connects to a data recorder 62d, such as the 21X Micro Logger, available from Campbell Scientific, Inc., of Logan, Utah. Example acceptable valves for valves 36d and 40d is the Model M28C-150VN valve sold by Atkomatic Valve Company of Indianapolis, Ind. Example materials for the various illustrated tubes and conduits would be ¼-inch polyethylene or some other suitable material.

Although the illustrated and described embodiments utilize a pressure transducer for measuring pressure within the various fluid chambers 24, alternate pressure take-offs such as below-grade gauges, might also be utilized. For example, a single-measurement device might be utilized having a mechanical pressure gauge connected in fluid communication with a fluid chamber 24. The device could be lowered within the earthen soil, and maintained there for an estimated time interval when hydraulic equilibrium with the surrounding soil would be reached. Upon a lapse of that time, the device could be quickly removed to surface and the pressure immediately is determined by looking at the gauge.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A tensiometer positioned within earthen soil for determining, in situ, a below grade soil moisture potential of the earthen soil, comprising:

an area of the earthen soil having a below grade portion, an above grade portion, and a bore formed in the earthen soil and which connects the above and below grade portions;

a housing received in the bore and having an upper end which is located proximate the above grade portion, and an opposite lower end which is located proximate the below grade portion;

a porous material tip mounted on the lower end of the housing and disposed in fluid communication therewith, the porous material tip placed in contact with the below grade portion, and wherein the porous material tip defines a first fluid chamber;

a first fluid conduit coupling in fluid communication the first fluid chamber and the lower end of the housing;

a second fluid conduit extending outwardly of the first fluid chamber;

a controllable isolation valve disposed in selectively fluid metering relation relative to the first fluid conduit, the controllable isolation valve mounted within the lower end of the housing, and entirely within the below grade portion, the controllable isolation valve mounted at a distance of less than 750 cm. from the first fluid chamber, and wherein the controllable isolation valve is operable from the above grade portion, and wherein the controllable isolation valve and the lower end of the housing define a second fluid chamber which is located at a distance of less than about 750 cm. from the first fluid chamber;

a source of degassed water constituting a reservoir received in the second fluid chamber, and wherein the controllable isolation valve allows the source of degassed water to pass through the first fluid conduit and into the first fluid chamber, and wherein the reservoir of degassed water is received entirely within the lower portion of the housing and cannot be visually inspected from the above grade portion; and a pressure transducer mounted in fluid communication with the second fluid conduit, the pressure transducer being entirely received within the lower end of the housing and operable to sense pressure changes resulting from the movement of the water from the first fluid chamber through the porous material tip and into the below grade portion of the earthen soil.

* * * * *